US006077842A

United States Patent [19]
Pamukcu et al.

[11] Patent Number: 6,077,842
[45] Date of Patent: Jun. 20, 2000

[54] METHOD OF INHIBITING NEOPLASTIC CELLS WITH PYRAZOLOPYRIDYLPYRIDAZINONE DERIVATIVES

[75] Inventors: Rifat Pamukcu, Spring House; Gary A. Piazza, Doylestown, both of Pa.

[73] Assignee: Cell Pathways, Inc., Horsham, Pa.

[21] Appl. No.: 09/200,376

[22] Filed: Nov. 24, 1998

[51] Int. Cl.⁷ .................................................. A01N 43/58
[52] U.S. Cl. ............................................................ 514/253
[58] Field of Search ............................................ 514/253

[56] References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schnettler et al. . |
| 3,812,127 | 5/1974 | Cronin et al. . |
| 3,819,631 | 6/1974 | Broughton et al. . |
| 3,865,840 | 2/1975 | Carson . |
| 3,920,636 | 11/1975 | Takahasi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,076,711 | 2/1978 | Ganguly et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,423,075 | 12/1983 | Dvornik et al. . |
| 4,457,927 | 7/1984 | Biere et al. . |
| 4,460,590 | 7/1984 | Möller . |
| 4,460,591 | 7/1984 | DeGraw et al. . |
| 4,863,902 | 9/1989 | Amagase et al. ........................ 514/12 |
| 4,880,810 | 11/1989 | Lowe, III et al. . |
| 4,885,301 | 12/1989 | Coates . |
| 4,923,874 | 5/1990 | McMahon et al. . |
| 4,971,972 | 11/1990 | Doll et al. . |
| 5,073,559 | 12/1991 | Coates . |
| 5,091,431 | 2/1992 | Tulshian et al. . |

(List continued on next page.)

FOREIGN PATENT DOCUMENTS

| | | |
|---|---|---|
| 0 330 004 A1 | 6/1989 | European Pat. Off. . |
| 0 347146 A2 | 12/1989 | European Pat. Off. . |
| 0 349239 A2 | 1/1990 | European Pat. Off. . |
| 0 351058 | 1/1990 | European Pat. Off. . |
| 0 352960 A2 | 1/1990 | European Pat. Off. . |
| 0 395328 A2 | 10/1990 | European Pat. Off. . |
| 0 428268 A2 | 5/1991 | European Pat. Off. . |
| 0 463756 A1 | 1/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 0 722937 A1 | 7/1996 | European Pat. Off. . |
| 0 743304 A1 | 10/1996 | European Pat. Off. . |
| 274218 | 12/1989 | German Dem. Rep. . |
| 3038166 | 4/1981 | Germany . |
| 56-53659 | 5/1981 | Japan . |
| 57-167974 | 10/1982 | Japan . |
| 8-311035 | 11/1996 | Japan . |
| 807826 | 1/1959 | United Kingdom . |
| 2063249 | 6/1981 | United Kingdom . |

(List continued on next page.)

OTHER PUBLICATIONS

Saini et al, "Biochemical and Molecular Mechanisms Regulating Apoptosis", Mol. Cell. Biochem. 178:9–25, Apr. 1998.

Rudin et al, "Apoptosis and Disease: Regulation and Clinical Relevance of Programmed Cell Death", Annu. Rev. Med. 48:267–81, Mar. 1997.

Chemical Abstracts 128:230381, "Preparation of Pyrazolopyridylpyridazinone Derivatives as Phosphodiesterase Inhibitors", Apr. 1998.

Chemical Abstracts 126:324740, "Pharmacokinetic Optimization of Cancer Chemotherapy. Effect on Outcomes", Apr. 1997.

Chemical Abstracts 126:207202, "Apoptotic Effects of Imidazo [1,2–a] pyrazine derivatives in the Human Dami Cell Line", Mar. 1997.

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti-inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

(List continued on next page.)

*Primary Examiner*—Frederick Krass
*Attorney, Agent, or Firm*—Robert W. Stevenson

[57] ABSTRACT

A method for inhibiting neoplasia, particularly cancerous and precancerous lesions by exposing the affected cells to pyrazolopyridylpyridazinone derivatives.

2 Claims, No Drawings

U.S. PATENT DOCUMENTS

| | | |
|---|---|---|
| 5,147,875 | 9/1992 | Coates et al. |
| 5,175,151 | 12/1992 | Afonso et al. |
| 5,223,501 | 6/1993 | Chakravarty et al. |
| 5,250,535 | 10/1993 | Verheyden et al. |
| 5,254,571 | 10/1993 | Coates et al. |
| 5,358,952 | 10/1994 | Moschel et al. |
| 5,376,683 | 12/1994 | Klar et al. |
| 5,393,755 | 2/1995 | Neustadt et al. |
| 5,401,774 | 3/1995 | Pamukcu et al. |
| 5,439,895 | 8/1995 | Lee et al. |
| 5,488,055 | 1/1996 | Kumar et al. |
| 5,614,530 | 3/1997 | Kumar et al. |
| 5,614,627 | 3/1997 | Takase et al. |
| 5,696,159 | 12/1997 | Gross et al. |
| 5,728,563 | 3/1998 | Tanaka |
| 5,756,818 | 5/1998 | Buchmann et al. |
| 5,852,035 | 12/1998 | Pamukcu et al. |
| 5,858,694 | 1/1999 | Piazza et al. |
| 5,874,440 | 2/1999 | Pamukcu et al. |

FOREIGN PATENT DOCUMENTS

| | | |
|---|---|---|
| WO 92/03419 | 3/1992 | WIPO. |
| WO 93/07149 | 4/1993 | WIPO. |
| WO 93/12095 | 6/1993 | WIPO. |
| WO 94/05661 | 3/1994 | WIPO. |
| WO 94/19351 | 9/1994 | WIPO. |
| WO 94/29277 | 12/1994 | WIPO. |
| WO 95 18969 | 7/1995 | WIPO. |
| WO 95/26743 | 10/1995 | WIPO. |
| WO 97/03070 | 1/1997 | WIPO. |
| WO 97/03985 | 2/1997 | WIPO. |
| WO 97/24334 | 7/1997 | WIPO. |
| WO 98/14448 | 4/1998 | WIPO. |
| WO 98/15530 | 4/1998 | WIPO. |
| WO 98/16224 | 4/1998 | WIPO. |
| WO 98/16521 | 4/1998 | WIPO. |
| WO 98/17668 | 4/1998 | WIPO. |
| WO 98/08848 | 5/1998 | WIPO. |
| WO 98/23597 | 6/1998 | WIPO. |
| WO 98/38168 | 9/1998 | WIPO. |
| WO 96/32379 | 10/1998 | WIPO. |

OTHER PUBLICATIONS

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'-Monophosphate and Guanosine Cyclic 3',5'-Monophosphate Phosphodiesterases, Molecular Pharmacology, 13, pp. 38–43 (1976).

Drees, Markus et al., 3',5'-Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor-x production and inhibition of cAMP phosphodiesterase activity, Immunology 78, pp. 520–525 (1993).

Mehta, Rajendra et al., Structure-Activity Relationships of Brassinin in Preventing the Development of Carcinogen-Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido-Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme-selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP-elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar-Kimber, K. et al., Modulation of TNFa and IL-1B from indotoxin-stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6-phenyl-3-(5-tetrazoly)pyridin-2(H)-one derivatives as cyclic AMP-dependent protein kinase agonists (Abstract Only), PCT Int. Appl. WO9206085 A1, (Sep. 26, 1991).

Molnar-Kimber, K. L. et al., Differential regulation of TNF-a and IL-1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme-selective phosphodiesterase inhibitors on ADP-induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1-methyl-3-isobutyl-8-(methylamino)xanthine (Abstract Only), Br. J. Pharmacol. 98(3) pp. 725–734 (1989).

Lichtner, Rosemarie B., The pyrimidopyrimidine derivatives RA233 and RX-RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1-(3-chloroanilino)-4-phenylpthalazine (MY-5445), a specific inhibitor of cyclic CMP phosphodiesterase, on human platelet aggregation (Abstract Only), J. Pharmacol. Exp. Ther. 229(2) pp. 467–471 (1984).

Ho-Sam Ahn et al., Potent Tetracyclic Guanine Inhibitors of PDE1 and PDE5 Cyclic Guanosine Monophosphate Phosphodiesterases with Oral Antihypertensive Activity; J. Med. Chem. 1997, 40, pp. 2196–2210.

J.A. Mitchell et al., Selectivity of nonsteroidal antiinflammatory drugs as inhibitors of constitutive and inducible cyclooxygenase; Proc. Natl. Acad. Sci. USA, vol. 90, Dec. 1994, pp 11693–11697.

J.D. Gaffen et al.: Increased killing of malignant cells by giving indomethacin with methotrexate, p. 30; col. 1; XP002084860Chemical Abstract, vol. 106, No. 11, Mar. 16, 1987, abstract No. 78377, J.D.

Tsou, K–C. et al. 5'-Nucleotide Phosphodiesterase Isozyme–V as a Marker for Liver Metastases in Breast Cancer Patients, Cancer 54:1788–1793, 1984.

Epstein P M et al.; Dep. Pharmacol., Univ. Tex. Med. Sch., M.D. Anderson Hosp., Houston, Tex. 88030, USA BIOSIS 78:140912, Increased Cyclic Nucleotide Phospho Di Esterase Activity Associated With Proliferation and Cancer in Human and Murine Lymphoid Cells.

Christian Schudt et al., "Phosphodiesterase Inhibitors" The Handbook of Immunopharmacology, Academic Press, 1996, pp. 65–134.

METHOD OF INHIBITING NEOPLASTIC CELLS WITH PYRAZOLOPYRIDYLPYRIDAZINONE DERIVATIVES

TECHNICAL FIELD

This invention relates to a method for the selective inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

In the breast, breast cancer is often treated surgically, often by radical mastectomy with its painful aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, sometimes referred to as "programmed cell death." Apoptosis naturally occurs in virtually all tissues of the body, and especially in self-renewing tissues such as bone marrow, immune cells, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of the high levels of cytotoxicity of the drugs, include hair loss, weight loss, vomiting, immune suppression and other toxicities. Therefore, there is a need to identify new drug candidates for therapy that do not have such serious side effects in humans.

In recent years, several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the prophylactic use of currently available NSAIDs, even in polyposis syndrome patients, is marked by severe side reactions that include gastrointestinal irritations, perforations, ulcerations and kidney toxicity. Once NSAID treatment is terminated due to such complications, the polyps return, particularly in polyposis syndrome patients.

Sulindac has been particularly well received among the NSAIDs for polyp treatment. Sulindac is a sulfoxide compound that itself is believed to be inactive as an anti-arthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to a sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below.

The compounds of that are useful in the methods of this invention include those of Formula I or pharmacologically acceptable salts thereof

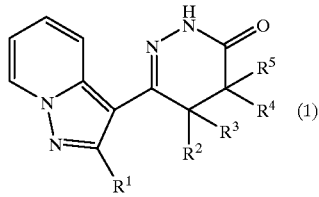

Formula (1)

wherein
$R^1$ is a lower alkyl group having 1–4 carbon atoms, or a cycloalkyl group having 3–6 carbon atoms;
$R^2$, $R^3$, $R^4$, and $R^5$ are independently selected from the group consisting of hydrogen, a lower alkyl group having 1–3 carbon atoms, or a phenyl group; or $R^3$ and $R^5$ may together form a double bond.

DETAILED DESCRIPTION OF THE PREFERRED EMBODIMENTS

As indicated above, this invention relates to a method for inhibiting neoplasia, particularly cancerous and precancerous lesions by exposing the affected cells to a compound of Formula I above.

Preferably, such compounds are administered without therapeutic amounts of an NSAID.

The present invention is also a method of treating mammals with precancerous lesions by administering a pharmacologically effective amount of an enterically coated pharmaceutical composition that includes compounds of Formula I.

Also, the present invention is a method of inhibiting the growth of neoplastic cells by exposing the cells to an effective amount of compounds of Formula I, wherein $R_1$ through $R_3$ etc. are defined as above.

In still another form, the invention is a method of inducing apoptosis in human cells by exposing those cells to an effective amount of compounds of Formula I to those cells sensitive to such a compound.

As used herein, the term "precancerous lesion" includes syndromes represented by abnormal neoplastic, including dysplastic, changes of tissue.

Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, and colon cancer.

As used herein, the term "neoplasm" refers to both precancerous and cancerous lesions.

It will also be appreciated that a compound of Formula I or a physiologically acceptable salt or solvate thereof can be administered as the raw compound, or as a pharmaceutical composition containing either entity.

Compounds useful in the methods of this invention are preferably formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories that may contain, in addition to the compounds of Formula I, excipients such as cocoa butter or a suppository wax.

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g. a box or bottle, or both) with suitable printed material (e.g. a package insert) containing indications, directions for use, etc.

The amount and frequency of administration may vary depending on the medication form, patient's age, patient's weight, and patient's conditions. Normally, 0.05~5 g/60 kg/day would be appropriate in an oral dosage form. As for intravenous administration, it is desirable not to exceed the daily amount in a oral form, which should be administered at a rate of 0.01~5 mg/kg/minute.

Examples of pharmacologically acceptable salts of the compounds expressed by general formula (1) in the present invention include salts with an acid such as hydrochloride, hydrobromate, citrate, methanesulfonate, and tartarate.

The term "lower alkyl group" represents a straight or branched hydrocarbon having 1–4 carbon atoms such as methyl, ethyl, or propyl. The term "cycloalkyl group" represents a cyclic hydrocarbon having 3–6 carbon atoms.

The production of compounds useful in the practice of this invention is described below and in WO98/14448, which is incorporated herein by reference.

To produce compounds of Formula I in which $R^3$ and $R^5$ do not form a double bond, i.e., compounds of formula (1a)

Formula (1a)

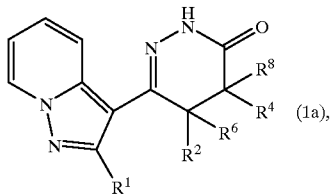

(wherein $R^1$ is the same as previously described; $R^2$, $R^4$, $R^6$, and $R^8$ could be the same or different, and each of them is a hydrogen atom, a lower alkyl group having 1–4 carbon atoms, or a phenyl group), a compound of formula (6) below is reacted with hydrazine, Formula (6)

(wherein $R^1$, $R^2$, $R^4$, $R^6$, and $R^8$ are the same as previously described.)

Such a reaction can take place as an example, in benzene, toluene, acetic acid, ethanol. The reaction temperature may be at room temperature or solvent reflux temperature, or therebetween. It is preferred to use ethanol as a reactive solvent and the heat reflux temperature as a reaction temperature.

The compounds in which $R^3$ and $R^5$ are bonded to each other and form a double bond, i.e., compounds of formula (1c)

Formula (1c)

(wherein $R^1$ $R^2$, and $R^4$ are the same as previously described), can reportedly be produced by oxidizing the compounds expressed by general formula (1b) below, Formula (1b)

wherein $R^1$, $R^2$, and $R^4$ are the same as previously described

It is preferred that the reaction takes place in an acetic acid solvent and bromine is used for the reaction. It is preferred that the reaction temperature be between 50–60 degrees Celsius.

The compounds expressed by the above general formula (6) can reportedly be produced using the three processes below.

Synthesis process 1

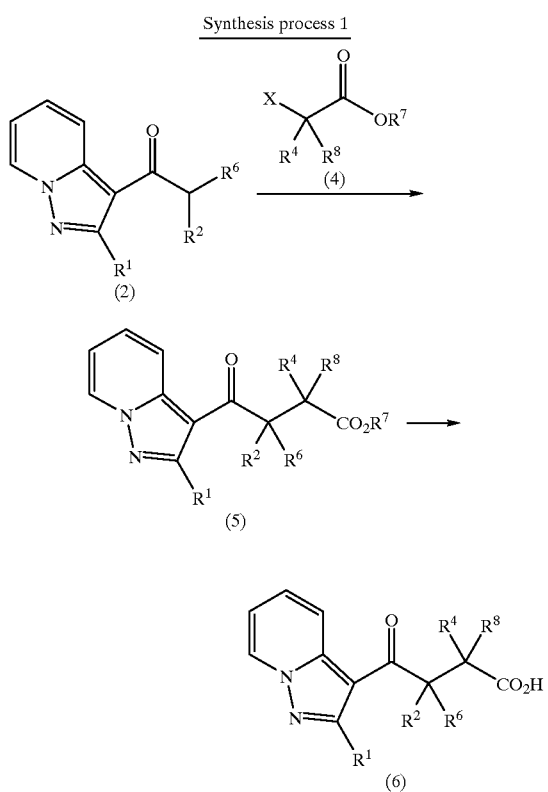

Synthesis process 2

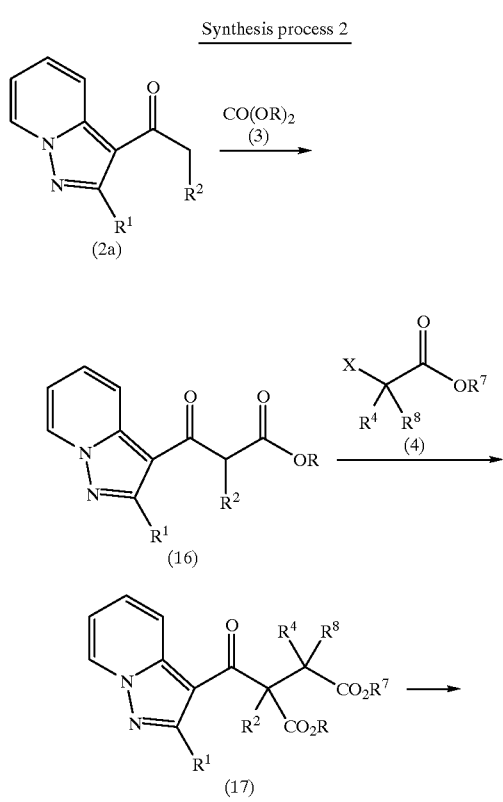

Synthesis process 3

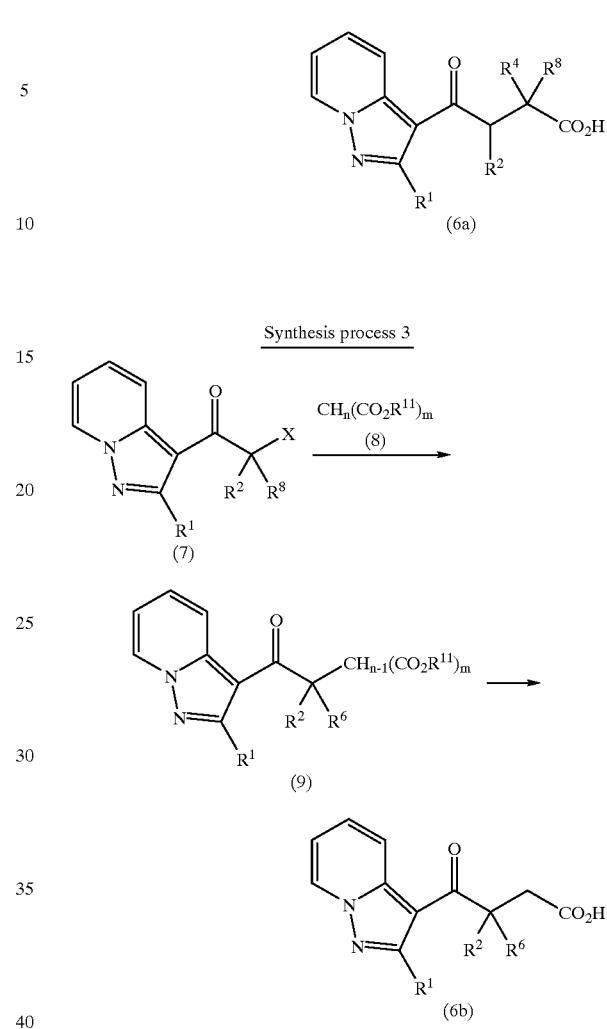

In synthesis process 1, the compounds expressed by general formula (5),

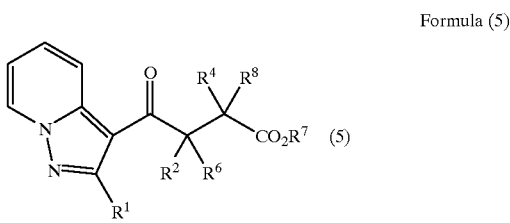

Formula (5)

wherein $R^1$, $R^2$, $R^4$, $R^6$, and $R^8$ are the same as previously described; and $R^7$ is a lower alkyl group having 1~3 carbon atoms,] can reportedly be obtained by reacting the compounds expressed by general formula (2) with the compounds expressed by general formula (4),

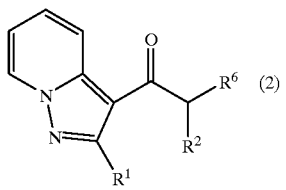

Formula (2)

[wherein $R^1$, $R^2$, and $R^6$ are the same as previously described,]

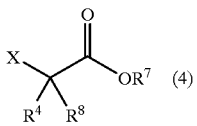

Formula (4)

and wherein X represents a halogen atom; and $R^4$, $R^7$, and $R^8$ are the same as previously described.

The reaction reportedly takes place under the presence of an inorganic base such as potassium t-butoxide or potassium hydride, or more preferably sodium hydride, using tetrahydrofuran, 1,4-dioxane, 1,2-dimethoxyethane, or even more preferably dimethylformamide as a reaction solvent. The reaction temperature is not particularly restricted. However, it is preferred that the reaction take place at 0 degree Celsius~the solvent reflux temperature.

In synthesis process 1, the compounds expressed by general formula (6),

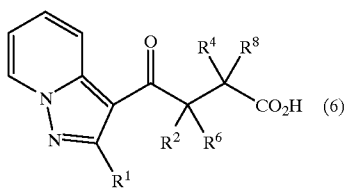

Formula (6)

wherein $R^1$, $R^2$, $R^4$, $R^6$, and $R^8$ are the same as previously described,] can be obtained by hydrolyzing the compounds expressed by general formula (5).

When the hydrolysis is performed with an acidic catalysis, it is preferred that it take place using hydrochloric acid or hydrobromic acid while the solution is heated to 80–120 degrees Celsius. Moreover, when the hydrolysis is performed with a basic catalysis, it is preferred that it take place using a sodium hydroxide aqua solution or a potassium hydroxide aqua solution with an alcohol solvent such as methanol or ethanol, or a solvent such as tetrahydrofuran or dimethylformamide at room temperature.

In synthesis process 2, the compounds expressed by general formula (16),

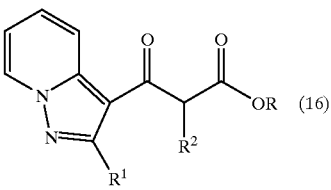

Formula (16)

wherein $R^1$ and $R^2$ are the same as previously described; and R is a lower alkyl group having 1~3 carbon atoms,] can be obtained by reacting the compounds expressed by general formula (2a) below, with the compounds expressed by general formula (3),

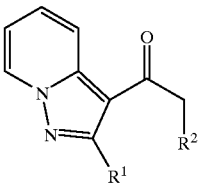

Formula (2a)

[wherein $R^1$ and $R^2$ are the same as previously described,]

$CO(OR)_2$ (3)

and wherein R is the same as previously described.

The reaction takes place under the presence of an inorganic base such as potassium t-butoxide or potassium hydride, or more preferably sodium hydride, using the compounds expressed by general formula (3) in the same amount as that of the solvent. As for the reaction temperature, it is preferred that this temperature is suitable for reflux by heating.

In synthesis process 2, the compounds expressed by general formula (17),

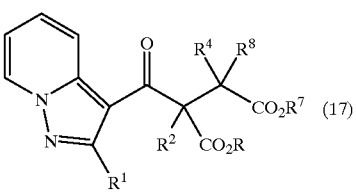

Formula (17)

wherein R, $R^1$, $R^2$, $R^4$, $R^7$, and $R^8$ are the same as previously described,] can be obtained by reacting the compounds expressed by general formula (16) with the compounds expressed by general formula (4),

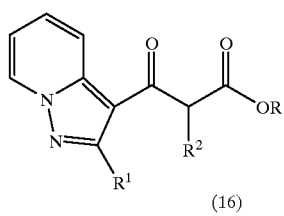

Formula (16)

[wherein R, R$^1$ and R$^2$ are the same as previously described,]

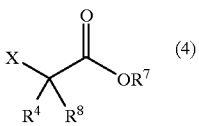

Formula (4)

and wherein X, R$^4$, R$^7$, and R$^8$ are the same as previously described.

The reaction takes place under the presence of an inorganic base such as potassium t-butoxide or potassium hydride, or more preferably sodium hydride, using tetrahydrofuran, 1,4-dioxane, 1,2-dimethoxyethane, or even more preferably dimethylformamide as a reaction solvent. The reaction temperature is not particularly restricted. However, it is preferred that the reaction take place at 0 degree Celsius~the solvent reflux temperature.

In synthesis process 2, the compounds expressed by general formula (6a),

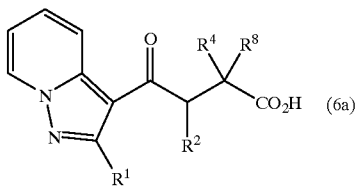

Formula (6a)

wherein R$^1$, R$^2$, R$^4$, R$^6$, and R$^8$ are the same as previously described,] can be obtained by hydrolyzing and decarboxylating the compounds expressed by general formula (17).

When the hydrolysis and decarboxylation are performed with an acidic catalysis, it is preferred that they take place using hydrochloric acid or hydrobromic acid while the solution is heated to 80–120 degrees Celsius. Moreover, when the hydrolysis and decarboxylation are performed with a basic catalysis, it is preferred that they take place using a sodium hydroxide aqua solution or a potassium hydroxide aqua solution with a alcohol solvent such as methanol or ethanol, or a solvent such as tetrahydrofuran or dimethylformamide at room temperature.

In synthesis process 3, the compounds expressed by general formula (9),

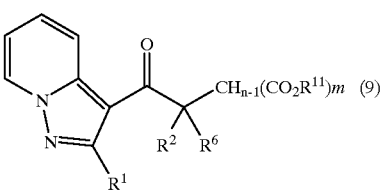

Formula (9)

wherein R$^1$, R$^2$ and R$^6$ are the same as previously described; R$^{11}$ is a lower alkyl group having 1~3 carbon atoms; and (n, m) is a combination of integers, (1, 3) or (2, 2),] can be obtained by reacting the compounds expressed by general formula (7) with the compounds expressed by general formula (8),

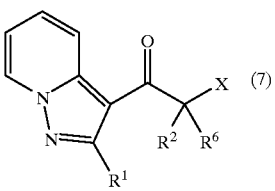

Formula (7)

wherein X, R$^1$, R$^2$ and R$^6$ are the same as previously described,] with the compounds expressed by general formula (8),

wherein the combination of (n, m) and R$^{11}$ are the same as previously described.

The reaction takes place under the presence of an inorganic base such as potassium t-butoxide or potassium hydride, or more preferably sodium hydride, using tetrahydrofuran, 1,4-dioxane, 1,2-dimethoxyethane, or even more preferably dimethylformamide as a reaction solvent. The reaction temperature is not particularly restricted. However, it is preferred that the reaction take place at 0 degree Celsius~the solvent reflux temperature.

In synthesis process 3, the compounds expressed by general formula (6b),

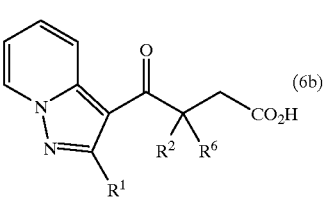

Formula (6b)

wherein R$^1$, R$^2$, and R$^6$ are the same as previously described,] can be obtained by hydrolyzing and decarboxylating the compounds expressed by the above general formula (9).

When the hydrolysis and decarboxylation are performed with an acidic catalysis, it is preferred that they take place with hydrochloric acid or hydrobromic acid while the solution is heated to 80~120 degrees Celsius. Moreover, when the hydrolysis and decarboxylation are performed with a basic catalysis, it is preferred that they take place using a sodium hydroxide aqua solution or a potassium hydroxide aqua solution with an alcohol solvent such as methanol or ethanol, or a solvent such as tetrahydrofuran or dimethylformamide at room temperature.

Moreover, when the compounds of the present invention have asymmetric carbon atoms at the fourth and fifth position of their dihydropyridazinone, optical isomers exist. These optical isomers are included in the practice of the methods of this invention.

The synthesis of the compounds of the invention and of the intermediates for use therein are illustrated by the following, non-limiting Examples from the aforesaid PCT application WO 98/14448.

EXAMPLE 1

3-Methyl-3-(2-Methylpyrazolo[1, 5-a]Pyridine-3-yl)-3-Oxopropionic Acid Methyl Ester

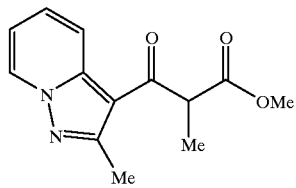

3-Methyl-3-propionylpyrazolo[1, 5-a]pyridine (5.28 g) is dissolved in dimethyl carbonate (100 ml). Then, sodium hydride (3.37 g) is added and the mixture is refluxed by heating for eight hours. As it is chilled in an ice bath, acetic acid is added. Subsequently water is added to dilute the solution. Then, extraction is performed using methylene chloride. After the organic layer is dried using anhydrous sodium sulfate, the solvent is removed under reduced pressure. The residuum is purified using silica gel column chromatography (developing solvent=ethyl acetate:n-hexane=1:3~1:1). The target material (5.13 g) is obtained in a yellow and oily form.

EXAMPLES 2–8

In a similar manner as in Example 1, the compounds listed below (Table 1) are obtained.

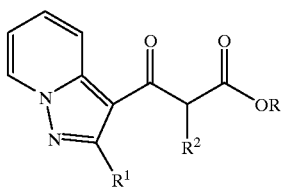

TABLE 1

| Example | $R^1$ | $R^2$ | R | Yield (%) | Properties |
|---|---|---|---|---|---|
| 2 | Me | Et | Me | 91 | Oily material with light yellow color |
| 3 | Et | Me | Me | 93 | Oily material with light yellow color |
| 4 | Pr | Me | Me | 54 | Oily material with yellow color |

TABLE 1-continued

| Example | $R^1$ | $R^2$ | R | Yield (%) | Properties |
|---|---|---|---|---|---|
| 5 | i-Pr | H | Me | 94 | Powder material with light yellow color |
| 6 | i-Pr | Me | Me | 91 | Oily material with brown color |
| 7 | i-Pr | Et | Me | 87 | Oily material with yellow color |
| 8 | cyclo-Pr | Me | Me | 46 | Oily material with brown color |

EXAMPLE 9

4-(2-Methylpyrazolo[1, 5a]Pyridine-3-yl)-3-Methoxycarbonyl-3-Methyl-4-Oxobutyric Acid Ethyl Ester

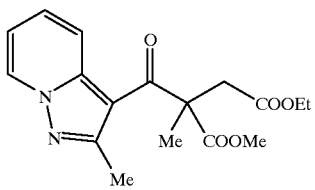

The compound of Example 1 (5.13 g) is dissolved in DMF (70 ml). Then, sodium (1.00 g) is added, and the mixture is stirred for 1 hour at room temperature. It is chilled in an ice bath. Ethyl 2-bromoacetate (2.77 ml) is added and the solution is stirred for 18 hours until its temperature reached room temperature. Subsequently a saturated ammonium chloride aqua solution is added. After water is added to dilute the solution, extraction is performed using ether. After the organic layer is washed with water and a saturated saline solution, it is dried using anhydrous sodium sulfate. Subsequently, the solvent is removed under reduced pressure and the residuum is purified using silica gel column chromatography (developing solvent=ethyl acetate:n-hexane=1:2). The target material (4.63 g) is obtained in a yellow and oily form.

EXAMPLE 10–16

In a similar manner as in Example 9, the compounds listed below (Table 2) are obtained, using ethyl 2-bromoacetate, or methyl 2-bromoacetate, or methyl 2-bromopropionate.

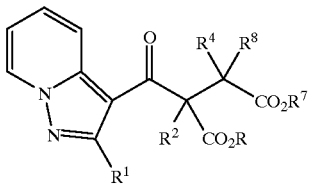

TABLE 2

| Example | R¹ | R² | R⁴ | R⁷ | R⁸ | R | Yield (%) | Properties |
|---|---|---|---|---|---|---|---|---|
| 10 | Me | Et | H | Me | H | Me | 78 | Oily material with light yellow color |
| 11 | Et | Me | H | Et | H | Me | 70 | Oily material with light yellow color |
| 12 | Pr | Me | H | Et | H | Me | 85 | Oily material with yellow color |
| 13 | i-Pr | H | Me | Me | H | Me | 77 | Powder material with light yellow color |
| 14 | i-Pr | Me | H | Et | H | Me | 69 | Oily material with brown color |
| 15 | i-Pr | Et | H | Et | H | Me | 69 | Oily material with yellow color |
| 16 | cyclo-Pr | Me | H | Et | H | Me | 37 | Oily material with brown color |

EXAMPLE 17

4-(2-Methylpyrazolo[1, 5-a]pyridine-3-yl)-3-methyl-4-oxobutyric Acid

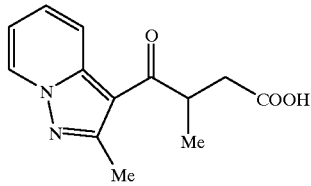

The compound of Example 9 (4.63 g) is dissolved in 47% hydrobromic acid (50 ml) and the solution is refluxed by heating for one hour. The solution is poured into an ice bath and extraction is performed using methylene chloride. After the organic layer is dried using anhydrous sodium sulfate, the solvent is removed under reduced pressure. The residuum is purified using silica gel column chromatography (developing solvent=methylene chloride:ethanol=10:1). The target material (2.76 g) is obtained in a purple powder form.

EXAMPLE 18–24

In a similar manner as in Example 17, the compounds listed below (Table 3) are obtained.

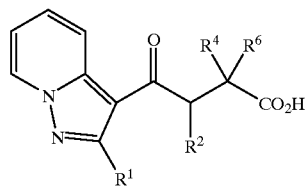

TABLE 3

| Example | R¹ | R² | R⁴ | R⁸ | Yield (%) | Properties |
|---|---|---|---|---|---|---|
| 18 | Me | Et | H | H | 75 | Oily material with light yellow color |
| 19 | Et | Me | H | H | 70 | Oily material with light yellow color |
| 20 | Pr | Me | H | H | 85 | Oily material with yellow color |
| 21 | i-Pr | H | Me | H | 77 | Powder material with light yellow color |
| 22 | i-Pr | Me | H | H | 69 | Oily material with brown color |
| 23 | i-Pr | Et | H | H | 69 | Oily material with yellow color |
| 24 | cyclo-Pr | Me | H | H | 37 | Oily material with brown color |

EXAMPLE 25

4-(2-Isopropylpyrazolo[1, 5-a]Pyridine-3-yl)-3-Phenyl-4-Oxobutyric Acid Methyl Ester

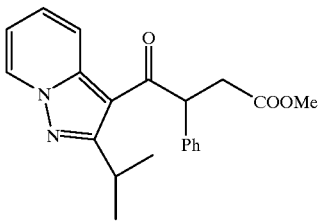

2-Isopropyl-3-phenacylpyrazolo[1, 5-a]pyridine (1.90 g) is dissolved in DMF (30 ml). Sodium hydride (0.35 g) is added and the mixture is stirred for 0.5 hours at room temperature. Then, 2-methyl bromoacetate (1.36 g) is added and the solution is stirred for 3 hours at room temperature. Subsequently, a saturated ammonium chloride aqua solution is added. After water is added to dilute the solution, extraction is performed using ether. The organic layer is washed with water and a saturated saline solution. Then, it is dried using anhydrous sodium sulfate. Subsequently, the solvent is removed under reduced pressure and the residuum is purified using silica gel column chromatography (developing solvent=ethyl acetate:n-hexane=1:3). The target material (1.58 g) is obtained in a yellow and oily form.

EXAMPLE 26

4-(2-Isopropylpyrazolo[1, 5-a]Pyridine-3-yl)-3-Phenyl-4-Oxobutyric Acid

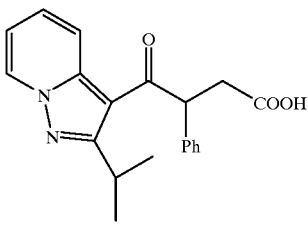

The compound of Example 25 (1.58 g) is dissolved in ethanol (15 ml). Then, 1-N sodium hydroxide (5 ml) is added and the mixture is stirred for 1 hour at room temperature. Water is added to the reaction solution. Subsequently, 10% hydrochloric acid is added to adjust its acidity to pH 3, and extraction is performed using methylene chloride. After the organic layer is dried using anhydrous sodium sulfate, the solvent is removed under reduced pressure. The target material (1.50 g) is obtained in a colorless powder form.

EXAMPLE 27

2,2-Diethoxycarbonyl-4-(2-Isopropylpyrazolo[1, 5-a]Pyridine-3-yl)-3-Methyl-4-Oxobutyric Acid Ethyl Ester

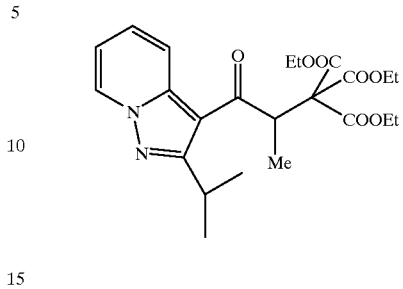

Triethoxycarbonylmethane (1.53 g) is dissolved in DMF (20 ml). Sodium hydride (0.28 g) is added and the mixture is stirred for 0.5 hours at room temperature. 3-(2-Bromopropionyl)-2-isopropylpyrazolo[1, 5-a]pyridine (1.77 g) is added and the solution is stirred for one hour at room temperature. Subsequently, it is stirred for 7 hours at 80~100 degrees Celsius. A saturated ammonium chloride aqua solution is added to the reaction solution. After water is added to dilute the solution, extraction is performed using ether. The organic layer is washed with water and a saturated saline solution. Then, it is dried using anhydrous sodium sulfate. Subsequently, the solvent is removed under reduced pressure and the residuum is purified using silica gel column chromatography (developing solvent=ethyl acetate:n-hexane=1:2). The target material (0.67 g) is obtained in a yellow and oily form.

EXAMPLE 28

2-Ethoxycarbonyl-4-(2-Isopropylpyrazolo[1, 5-a]Pyridine-3-yl)-4-Oxobutyric Acid Ethyl Ester

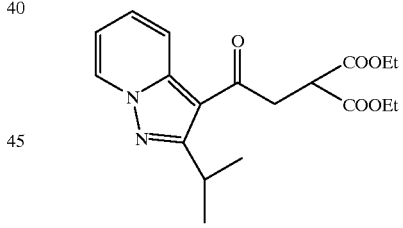

Sodium (0.10 g) is dissolved in ethanol (4 ml). Then, diethyl malonate (0.71 g) is added at room temperature. After the mixture is stirred for 20 minutes at 50 degrees Celsius, an ethanol solution (6 ml) of 3-(2-bromoacetyl)-2-isopropylpyrazolo[1, 5-a]pyridine (1.06 g) is added and the solution is stirred for 75 minutes at 80 degrees Celsius. The reaction solution is concentrated. Water and ethyl acetate are added to the residuum and the organic layer is separated. After the organic layer is washed with water and a saturated saline solution, it is dried using anhydrous sodium sulfate. Subsequently, the solvent is removed under reduced pressure and the residuum is purified using silica gel column chromatography (developing solvent=ethyl acetate:n-hexane=1:3). The target material (0.44 g) is obtained in a powder form with a light yellow color.

EXAMPLE 29

4-(2-Isopropylpyrazolo[1, 5-a]Pyridine-3-yl)-3-Methyl-4-Oxobutyric Acid

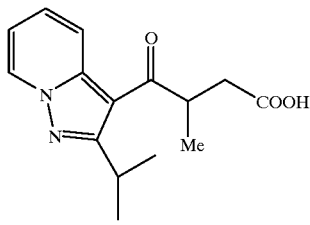

In a similar manner as in Example 17, the same compound (0.31 g) as the target compound in Example 21 is obtained in an amorphous form with a light yellow color using the compound (0.67 g) of Example 27.

EXAMPLE 30

4-(2-Isopropylpyrazolo[1, 5-a]Pyridine-3-yl)-4-Oxobutyric Acid

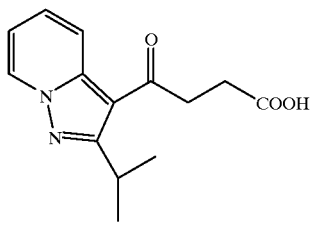

In a similar manner as in Example 17, the target compound (0.52 g) is obtained in a colorless powder form using the compound (0.72 g) of Example 28.

EXAMPLE 31

6-(2-Methylpyrazolo[1, 5-a]Pyridine-3-yl)-5-Methyl-4.5-Dihydro-3(2H)-Pyridazinone

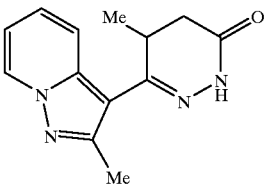

The compound of Example 17 (2.76 g) and hydrazine monohydrate (0.90 g) are dissolved in ethanol (30 ml) and the solution is refluxed by heating for three hours. The solvent is removed from the reaction solution under reduced pressure. The residuum is purified using silica gel column chromatography (developing solvent=methyl chloride:ethanol=10:1). The target material (2.04 g) is obtained in a colorless powder form. Recrystallization of this material in isopropyl ether produced colorless prism-shaped crystals. The melting point is 146~147 degrees Celsius.

| Elemental analysis values (%): As $C_{13}H_{14}N_4O$ | | | |
|---|---|---|---|
| | C | H | N |
| Calculated values: | 64.45 | 5.82 | 23.12 |
| Reported values: | 64.28 | 5.87 | 22.84 |

EXAMPLE 32–40

In a similar manner as in Example 31, the compounds listed below (Table 4) are obtained.

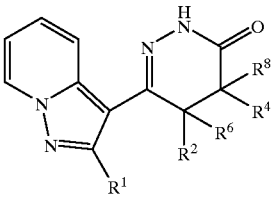

TABLE 4

| Example | $R^1$ | $R^2$ | $R^4$ | $R^6$ | $R^8$ | Yield (%) | Melting Point (° C.) (Recrystallization solvent) | Elemental Analysis Values Calculated values/ Reported values C, H, N |
|---|---|---|---|---|---|---|---|---|
| 32 | Me | Et | H | H | H | 80 | 138~140 i-Pr2O | $C_{14}H_{16}N_4O$ 65.61 6.29 21.86 65.70 6.31 21.72 |
| 33 | Et | Me | H | H | H | 79 | 131~132 i-Pr2O | $C_{14}H_{16}N_4O$ 65.61 6.29 21.86 65.74 6.22 21.85 |
| 34 | Pr | Me | H | H | H | 66 | 141~142 i-Pr2O | $C_{15}H_{11}N_4O$ 66.65 6.71 20.73 66.43 6.64 20.50 |
| 35 | i-Pr | H | H | H | H | 86 | 213.5~215.5 EtOH | $C_{14}H_{16}N_4O$ 65.61 6.29 21.86 65.33 6.31 21.70 |

TABLE 4-continued

| Example | R[1] | R[2] | R[4] | R[6] | R[8] | Yield (%) | Melting Point (° C.) (Recrystallization solvent) | Elemental Analysis Values Calculated values/ Reported values C, H, N |
|---|---|---|---|---|---|---|---|---|
| 36 | i-Pr | Me | H | H | H | 50 | 119~122 i-Pr2O | $C_{15}H_{11}N_4O$ 66.65 6.71 20.73 66.54 6.73 20.67 |
| 37 | i-Pr | Et | H | H | H | 77 | 147 i-Pr2O | $C_{16}H_{20}N_4O$ 67.58 7.09 19.70 67.47 7.05 19.62 |
| 38 | i-Pr | Ph | H | H | H | 55 | 192~193 i-Pr2O | $C_{20}H_{20}N_4O$ 71.49 6.12 16.67 71.81 6.25 16.27 (1/5 $H_2O$ adduct) |
| 39 | i-Pr | H | Me | H | H | 86 | 207~208 EtOH | $C_{15}H_{13}N_4O$ 66.65 6.71 20.73 66.65 6.58 20.74 |
| 40 | cyclo-Pr | Me | H | H | H | 79 | 134 i-Pr2O | $C_{15}H_{16}N_4O$ 67.15 6.01 20.88 67.31 6.07 20.85 |

EXAMPLE 41

6-(2-Methylpyrazolo[1, 5-a]Pyridine-3-yl)-5-Methyl-3(2H)-Pyridazinone

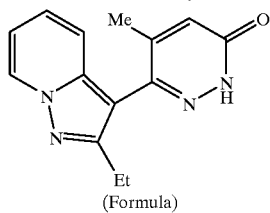

(Formula)

The compound of Example 36 (1.00 g) is dissolved in acetic acid (30 ml). As it is being stirred, bromine (0.22 ml) is added. The solution is stirred for 0.5 hours. The reaction solution is poured into water. Extraction is performed using methylene chloride. After the organic layer is washed with water and a saturated sodium hydrogencarbonate aqua solution, it is dried using anhydrous sodium sulfate. Then, the solvent is removed from the reaction solution under reduced pressure. The residuum is purified using silica gel column chromatography (developing solvent=methyl chloride:ethanol=15:1). The target material (0.69 g) is obtained in a powder form with a light purple color. Recrystallization of this material in ethyl acetate produced prism-shaped crystals with a light purple color. The melting point is 216~217 degrees Celsius.

| Elemental analysis values (%): As $C_{14}H_{14}N_4O$ | | | |
|---|---|---|---|
| | C | H | N |
| Calculated values: | 66.13 | 5.55 | 22.03 |
| Reported values: | 65.96 | 5.49 | 21.90 |

EXAMPLE 42–43

In a similar manner as in Example 41, the compounds listed below (Table 5) are obtained.

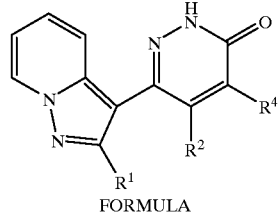

FORMULA

TABLE 5

| Example | R[1] | R[2] | R[4] | Yield (%) | Melting Point (° C.) (Recrystallization solvent) | Elemental Analysis Values Calculated values/Measured values C, H, N |
|---|---|---|---|---|---|---|
| 42 | i-Pr | H | Me | 71 | 216~217 AcOEt | $C_{15}H_{16}N_4O$ 67.15 6.01 20.88 66.95 5.97 20.82 |
| 43 | i-Pr | H | H | 73 | 134 AcOEt | $C_{14}H_{14}N_4O$ 65.66 5.59 21.88 65.43 5.56 21.64 (1/10 $H_2O$ adduct) |

EXAMPLE 44

(−)-6-(2-Isopropylpyrazolo[1, 5-a]Pyridine-3-yl)-5-Methyl-4,5-Dihydro-3(2H)-Pyridazinone and (+)-6-(2-Isopropylpyrazolo[1, 5-a]Pyridine-3-yl)-5-Methyl-4,5-Dihydro-3(2H)-Pyridazinone The compound of Example 36 (1.36 g) is dissolved in a 65 ml mixture of ethanol and hexane (1:4). This solution is automatically fractionated using HPLC (optical division column manufactured by Chiralcell OD Daiseru Kagaku Kougyou: the transport layer=hexane:isopropanol=9:1, the poured amount=1 ml, flow rate=24 ml/minute, detection wavelength=293 nm). The compounds in each of the obtained fractions are recrystallized using diisopropyl ether. From the earlier fractions, 530 mg of the (−) isomer is obtained as a colorless powder form, and from the latter fractions, 560 mg of the (+) isomer is obtained as a colorless powder form.

| | | | |
|---|---|---|---|
| The (−) isomer: | Melting point = 164~165 degrees Celsius Angle of rotation $[\alpha]_D^{34} = -179$ (C = 0.24, CHCl$_3$) | | |
| Elemental analysis values (%): | As $C_{15}H_{18}N_4O$ | | |
| | C | H | N |
| Calculated values: | 66.66 | 6.71 | 20.73 |
| Measured values: | 66.50 | 6.64 | 20.67 |
| The (+) isomer: | Melting point = 164~165 degrees Celsius Angle of rotation $[\alpha]_D^{34} = +179$ (C = 0.24, CHCl$_3$) | | |
| Elemental analysis values (%): | As $C_{15}H_{18}N_4O$ | | |
| | C | H | N |
| Calculated values: | 66.66 | 6.71 | 20.73 |
| Measured values: | 66.26 | 6.75 | 20.48 |

It will be understood that various changes and modifications can be made in the details of procedure, formulation and use without departing from the spirit of the invention, especially as defined in the following claims.

We claim:

1. A method of treating a mammal having precancerous lesions comprising administering to said mammal a pharmacologically effective amount of a compound of Formula I or pharmaceutically acceptable salt thereof:

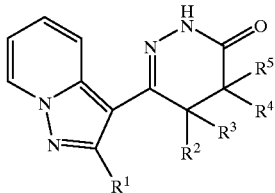

(1)

wherein $R^1$ is a lower alkyl group having 1–4 carbon atoms, or a cycloalkyl group having 3–6 carbon atoms;

$R^2$, $R^3$, $R^4$, and $R^5$ are independently selected from the group consisting of hydrogen, a lower alkyl group having 1–4 carbon atoms, and a phenyl group; or $R^3$ and $R^5$ together form a double bond, wherein said mammal is sensitive to said compound.

2. A method for inhibiting the growth of neoplastic cells comprising exposing the cells to a growth inhibiting effective amount of a compound of Formula I or pharmaceutically acceptable salt thereof:

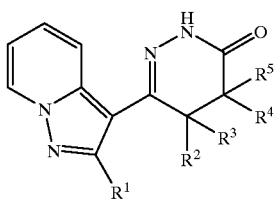

(1)

wherein $R^1$ is a lower alkyl group having 1–4 carbon atoms, or a cycloalkyl group having 3–6 carbon atoms;

$R^2$, $R^3$, $R^4$, and $R^5$ are independently selected from the group consisting of hydrogen, a lower alkyl group having 1–4 carbon atoms, and a phenyl group; or $R^3$ and $R^5$ together form a double bond, wherein said cells are sensitive to said compound.

* * * * *